(12) United States Patent
Johannessen et al.

(10) Patent No.: US 8,834,603 B2
(45) Date of Patent: Sep. 16, 2014

(54) METHOD FOR DETERMINING THE DEGREE OF SATURATION OF SOLID AMMONIA STORAGE MATERIALS IN CONTAINERS

(75) Inventors: Tue Johannessen, Glostrup (DK); Johnny Johansen, Kobenhavn S (DK); Jacob Hjerrild Zeuthen, Birkerod (DK); Henning Schmidt, Dyssegard (DK); Ulrich Joachim Quaade, Bagsvaerd (DK)

(73) Assignee: Amminex Emissions Technology A/S, Soborg (DK)

( * ) Notice: Subject to any disclaimer, the term of this patent is extended or adjusted under 35 U.S.C. 154(b) by 221 days.

(21) Appl. No.: 13/579,375

(22) PCT Filed: Feb. 14, 2011

(86) PCT No.: PCT/EP2011/000674
§ 371 (c)(1), (2), (4) Date: Oct. 24, 2012

(87) PCT Pub. No.: WO2011/103968
PCT Pub. Date: Sep. 1, 2011

(65) Prior Publication Data
US 2013/0209316 A1    Aug. 15, 2013

Related U.S. Application Data

(60) Provisional application No. 61/308,018, filed on Feb. 25, 2010.

(30) Foreign Application Priority Data

Feb. 25, 2010  (EP) .................................. 10001955

(51) Int. Cl.
F17C 11/00    (2006.01)
C01C 1/00     (2006.01)

(52) U.S. Cl.
USPC .................. 95/15; 96/112; 96/113; 206/0.7; 423/352

(58) Field of Classification Search
USPC ............ 96/109, 112, 113, 146; 95/14, 15, 18, 95/19, 128; 206/0.7; 423/352
See application file for complete search history.

(56) References Cited

U.S. PATENT DOCUMENTS 8,088,201 B2 *   1/2012   Johannessen ................... 96/108
8,449,857 B2 *   5/2013   Johannessen et al. ........ 423/352
(Continued)

FOREIGN PATENT DOCUMENTS

DE    10 2006 061 370    6/2008
DE    10 2008 002 612    12/2009
(Continued)

OTHER PUBLICATIONS

Johannessen, T., et al., "Ammonia Storage and Delivery Systems for Automotive NOx Aftertreatment", SAE Technical Paper Aeries, Societe of Automotive Engineers, vol. SP-2154, No. 2008-01-1027, Apr. 14, 2008.

Primary Examiner — Frank Lawrence
(74) Attorney, Agent, or Firm — Frost Brown Todd LLC (57) ABSTRACT

A method is provided for estimating the degree of saturation (S) of a reversible solid ammonia storage material (3) in a storage unit (1). The storage unit (1) is equipped with a heater (2) to release ammonia and a connected tube (4) for ammonia flow. The initial temperature ($T_{INIT}$) is measured with a sensor (9) in or around the storage unit (1) before any heating is initiated. Heating is initiated while recording the active time of heating (t) or the amount of energy (Q) released by the heater. The desorption pressure created by solid storage material in the storage unit (1) is measured via a pressure sensor (8) in fluid communication with the storage unit (1). The time ($t_{TARGET}$), or the heat ($Q_{TARGET}$) where the pressure reaches a certain target pressure ($P_{TARGET}$) is recorded. The values of the target-pressure time ($t_{TARGET}$), or the target-pressure heat ($Q_{TARGET}$), and the initial temperature ($T_{INIT}$) are used to compute an approximate degree of saturation (S).

16 Claims, 6 Drawing Sheets

(56) References Cited

U.S. PATENT DOCUMENTS

| | | |
|---|---|---|
| 8,473,226 B2 * | 6/2013 | Quaade .................... 702/55 |
| 8,551,219 B2 * | 10/2013 | Johannessen et al. ......... 95/128 |
| 2001/0053342 A1 * | 12/2001 | Marko et al. ................. 423/235 |
| 2010/0021780 A1 * | 1/2010 | Johannessen et al. ......... 429/19 |
| 2010/0062296 A1 | 3/2010 | Johannessen |
| 2011/0283677 A1 | 11/2011 | Kaefer |
| 2012/0288774 A1 * | 11/2012 | Johannessen et al. ........ 429/416 |

FOREIGN PATENT DOCUMENTS

| | | |
|---|---|---|
| EP | 1 992 397 | 11/2008 |
| WO | WO 2006/012903 | 2/2006 |
| WO | WO 2008/077652 | 7/2008 |
| WO | WO 2009/156204 | 12/2009 |

\* cited by examiner

FIGURE 6

METHOD FOR DETERMINING THE DEGREE OF SATURATION OF SOLID AMMONIA STORAGE MATERIALS IN CONTAINERS

FIELD OF THE INVENTION

This invention relates to the application of solid ammonia storage materials as sources for ammonia in an ammonia consuming process. Ammonia is made available from a rechargeable solid storage material by controlled thermal desorption from the solid by means of heating. In particular, the invention relates to a method whereby an approximate saturation level of the storage material is determined by a procedure during start-up. This enables functionality similar to the filling level of a liquid tank.

BACKGROUND OF THE INVENTION

Ammonia is a widely used chemical with many applications. One specific application is as reductant for selective catalytic reduction (SCR) of $NO_x$ in exhaust gas from combustion processes.

For most applications, and in particular in automotive applications, the storage of ammonia in the form of a pressurized liquid in a vessel is too hazardous. Urea is a safe, but an indirect and impractical method for mobile transport of ammonia since it requires urea to be transformed into ammonia by a process involving spray, evaporation, thermolysis and hydrolysis $((NH_2)_2CO+H_2O \rightarrow NH_3+CO_2)$, which is difficult to achieve under driving conditions with low engine load or cold weather.

A storage method involving ad- or absorption of molecular ammonia in a solid can circumvent the safety hazard of anhydrous liquid ammonia and eliminate the problem with decomposition of a liquid reductant.

Metal ammine salts are ammonia absorbing and desorbing materials, which can be used as solid storage media for ammonia (see, e.g. WO 2006/012903 A2), which, in turn, as mentioned above, may be used as the reductant in selective catalytic reduction to reduce $NO_x$ emissions.

For the use as ammonia source for automotive NOx reduction, the demands for the functionality are tightly linked to emission legislation and dynamic operation under real driving conditions. Ammonia Storage and Delivery Systems—hereafter abbreviated ASDS—have to be able to deliver ammonia shortly after engine start to enable vehicle certification according to e.g. European and US driving cycles.

WO 2008/077652 A2 discloses a method and device that allows for rapid availability of ammonia from a solid storage material by having a system with two main functionalities: A small, operational unit heated by e.g. electricity and a larger ammonia storage unit that is used as a source to carry out on-board resaturation of the small unit. The method and device can have at least two types of configurations:

- if the material in the smaller unit has a higher binding strength for ammonia absorption than the material in the large unit, then the smaller unit can passively absorb ammonia from the big tank after operation—even if the larger unit is not heated.
- If the materials in the two tanks are the same, then the larger tank is equipped with means for heating that provides the opportunity to reach suitable desorption pressure from the main tank to resaturate the smaller unit.

What remains for optimizing such a system is to be able to determine when to carry out the resaturation of the smaller storage unit—or more directly a methodology that gives the same type of functionality as a liquid level sensor in a tank. One way of finding out that a (smaller) storage unit requires resaturation (from a larger unit) is when it is empty. Materials that absorb ammonia typically have well-defined relationship between temperature and desorption pressure and if a required desorption pressure cannot be established at a certain temperature, then the storage material is depleted of ammonia—just like one cannot create pressure of steam in a boiler if the unit does not contain any water WO 2009/156204 A1 discloses a system similar to WO 2008/077652 A2 but with an added feature that the small storage unit is determined as empty by using pressure measurement and the temperature of the storage unit. However, it is not clear whether such a method works really satisfactory Therefore, there is a desire for a new method enabling the degree of saturation of ammonia in a container loaded with a material capable of absorption and desorption of ammonia to be determined or estimated. This method should preferably not introduce new, costly equipment in the system.

SUMMARY OF THE INVENTION

The invention relates to a method for determining the saturation level in a solid ammonia storage unit that is used as an ammonia source for an ammonia consuming process, e.g. selective reduction of $NO_x$ in a vehicle with an internal combustion process. The ammonia is made available from the storage material via thermal desorption by heating the storage unit. The degree of saturation, S (S=0 is empty and S=1 or S=100% is full) can be determined during each cold start phase, e.g. the first 0.1-10 minutes when the storage unit is being heated after a certain period of time without use. The method of determining S involves:

- Establish knowledge of the initial temperature of the unit, $T_{INIT}$. This temperature may simply be the temperature of the surroundings measured elsewhere on the application (vehicle) using the storage unit if the unit has been in non-operating mode for a certain period of time, e.g. 30 minutes or more.
- Initiate the heating of the unit and start recording the duration of the active heating time (e.g. measured in seconds of heating). Alternatively, the active heating time may be accounted for by accumulated energy (e.g. joules or Watt-hours of energy input, Q) if the heater does not have a constant power output at constant voltage supply, such as a PTC heating element.
- Measure the desorption pressure created by the solid storage material undergoing a raise in temperature—discretely or continuously—as a function of time during the heat-up period.
- Record the time, $t_{TARGET}$ (or alternatively $Q_{TARGET}$), when a given pressure target, $P_{TARGET}$, is reached.
- Use the values of $t_{TARGET}$ and $T_{INIT}$ to compute an approximate degree of saturation, S.

General Description

It has been recognized that during the transient conditions of start-up after initiation of heating, the temperature is not constant and the material may be partly saturated. As a consequence, in a method as disclosed in WO 2009/156204 A1 mentioned in the background section the measurement of pressure and the output from a temperature sensor in (or next to) the storage material can hardly be used for sufficiently determining the degree of saturation. Such a method only allows determining when the unit is empty—not how close it is to being empty. Another difficulty with such a method is that the small storage unit will have long start-up times (may be unacceptable long) during the last cycles before regeneration because one cannot really evaluate when a start-up unit would not perform well under start-up in the next cold start. Lastly, full renaturation of the smaller storage unit may not be obtained always and the known method would lack the ability to determining how much ammonia was transferred back into the smaller unit from the main storage unit. That may further add to the uncertainty of the degree of saturation of the smaller storage unit.

The use the values of $t_{TARGET}$ and $T_{INIT}$ to compute an approximate degree of saturation S may be based on a model or an algorithm describing the storage unit, e.g. in the form of expected or experimental mapping data or a look-up table. A set of experimental mapping data or look-up table may be generated for a prototype of the storage unit, or even specifically for the individual unit in question.

This estimation of S can be used for (but not limited to) the following features:

If S is below a critical level, i.e. where it is anticipated that proper start-up time within legislative requirements cannot be achieved on next cold start, the resaturation of the (partly) depleted storage unit is initiated by heating of one or more additional storage units to obtain a proper driving force for resaturation of the (partly) depleted unit with a too low S-value.

The knowledge of S can be used for on-board diagnostics (OBD) for e.g. automotive industry where there are certain requirements for knowing the operational state of functional hardware related to the emissions control system of a vehicle powered by an internal combustion engine.

This invention is particularly advantageous in cases where the storage unit is not reaching a state of complete resaturation, which will almost always be the case in real applications, after a main storage tank has been heated to provide a suitable pressure for reabsorbing ammonia since it allows determining the obtained S-value after an resaturation event and not just relying on an assumption that S=1 is reached.

Some embodiments have a specific configuration of a storage unit where the heating element is placed inside (or embedded by) the storage material whereby the storage material becomes an insulator towards the surroundings. This also provides improved opportunities reducing the power consumption during operation and to improve the resaturation afterwards because re-absorption in the unit releases heat that has to be dissipated away from the unit. The resaturation is much slower if the heating was done from the outside because insulation outside of the heating would be required but that at the same time would have a negative effect on resaturation.

A special feature of internal heating is that it has been found that the link between $t_{TARGET}$ and S is more well-defined if the heater is inside the unit because all the energy input is dissipated to the storage material before heat is lost to the surroundings. Thus, the estimation of S can be done with greater accuracy.

According to another optional feature the knowledge of S may be important for very long driving distances whereby there is a risk that the smaller unit is running out of ammonia or crossing the critical level saturation level during the driving period. After having estimated S during start-up, an algorithm may additionally consist of:

During the driving after the start-up period (where $t_{TARGET}$ or $Q_{TARGET}$ was measured and S was estimated), the amount of dosed ammonia is computed and subtracted from the estimated S-value to have a real-time parameter for the decreasing degree of saturation. The value of S at the end of the driving period may be compared with the value obtained in the next start-up phase, i.e. that the actual value of S is stored in the model/algorithm/controller.

During extended driving period, the S-parameter is reduced because of the dosing of ammonia. The controller can determine if a critical level of S is reached during the operation and the additional storage unit requires activation by heating. This prevents the situation that the smaller unit is degassed below a level where suitable start-up times can be obtained on the next cold start.

Other features and use of the method in similar applications that require the knowledge of the parameter S are inherent in the methods disclosed or will become apparent to those skilled in the art from the following detailed description of embodiments and its accompanying drawings.

DESCRIPTION OF EMBODIMENTS

Figure 1A:
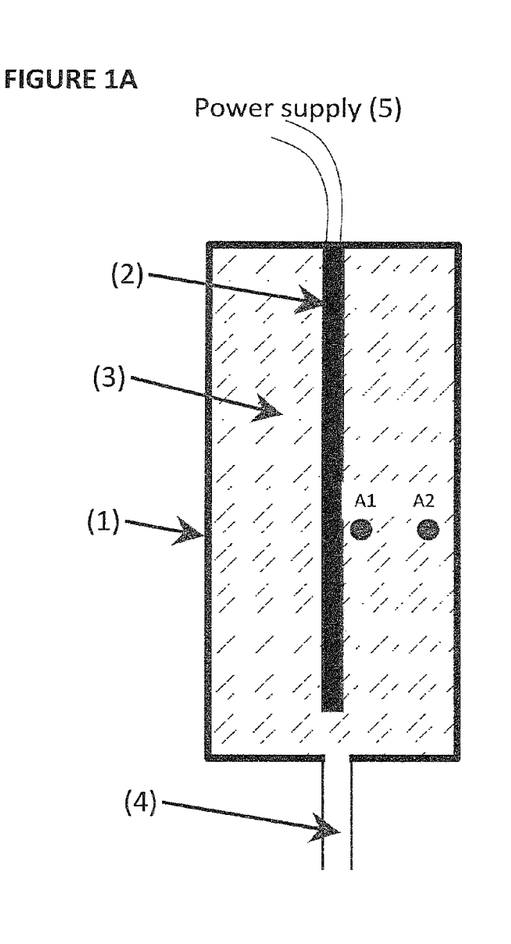
FIG. 1 (A+B) shows an example of an embodiment of the invention. Parts A and B refer to two different states of saturation: Full saturation (A) and partly saturated (B). The legends A1, A2, B1 and B2 refer to certain locations in the storage material.

FIG. 1A shows an example of a device where the present inventions is can be applied. A storage container 1, which can be made of e.g. steel or aluminum, contains a heating element 2 inside the storage material 3 and the container has an exit tube 4 that allows ammonia to flow out during desorption by heating and it also allows for providing a pressure of ammonia from a different source, e.g. a larger storage container 10 (FIG. 6) to resaturate the storage material. The heater can be an electrical heater that has a power supply 5. The pressure measurement is done with a pressure sensor 8 (shown on FIG. 6) that is connected to the tube 4.

Figure 1B:
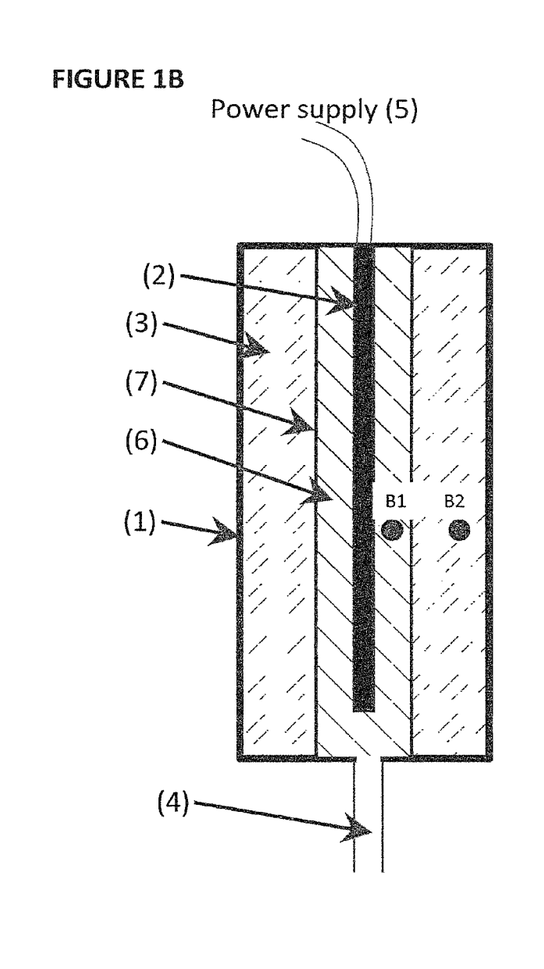

FIG. 1B shows the same unit but here the storage material is partly degassed after some of the ammonia has been desorbed by heating of the unit. The degassed part 6 is typically present closest to the heating source and the saturated material 3 is further away from the heating source. The line 7 illustrates a front where the material is fully saturated on one side 3 and partly or fully degassed on the other side 6. In reality, such a sharp front is not present but the overall degree of saturation can be computed as a weighted average over the entire container. For example, the storage container 1 makes ammonia available for NOx conversion in a selective catalytic reduction (SCR) catalyst 16 (included in FIG. 6) in the exhaust 15 (shown in FIG. 6) of a vehicle, e.g. driven by a Diesel engine 14 (shown in FIG. 6).

In the introduction, it was mentioned that a simple temperature measurement linked to desorption pressure from the solid cannot be used for determining S and this is evident from FIG. 1. Two locations in the solid are illustrated: A1 and B1 being close to the heater and A2 and B2 are far from the heating source. It can be seen that having a temperature sensor either inside the heater, on the wall of the container or as example in points A1/B1 or A2/B2 would not give a well-defined opportunity to link thermodynamics (temperature and pressure relationship of an absorption material) to a degree of saturation. There would always be gradients present in the container during heating and a certain temperature level could not be linked to a well-defined homogeneous temperature of the material providing ammonia pressure by desorption.

The hypothesis of the invention is that the gradual degassing of the ammonia from a storage unit will increase the heat-transfer distance from a heater to the material that is partly or fully saturated and that this will introduce a well-define time-delay from the time of initiating the heating to the point in time where the moving temperature front reaches the saturated material Another hypothesis of the invention is that this time-delay will have a unique relationship also with the initial temperature of the storage unit before the heating starts. Both hypotheses have to be fulfilled in order to make the invention work under all relevant conditions of e.g. a vehicle where the storage unit is used to make ammonia available for NOx conversion by SCR shortly after a cold-start of the vehicle.

The link to a possible method for estimating the degree of saturation can then be made if the storage unit under almost all combinations of initial temperature, $T_{INIT}$ and degree of saturation, S, has a unique value (or well-defined interval) of the heating time required, $t_{TARGET}$ for reaching a certain desired pressure level, $P_{TARGET}$. This pressure level can be measured by a standard pressure sensor 8 (FIG. 6) and such a sensor would have to be present for such an application of the solid material because of the control of the heating of the unit after the initial warm-up period is over.

Figure 2:
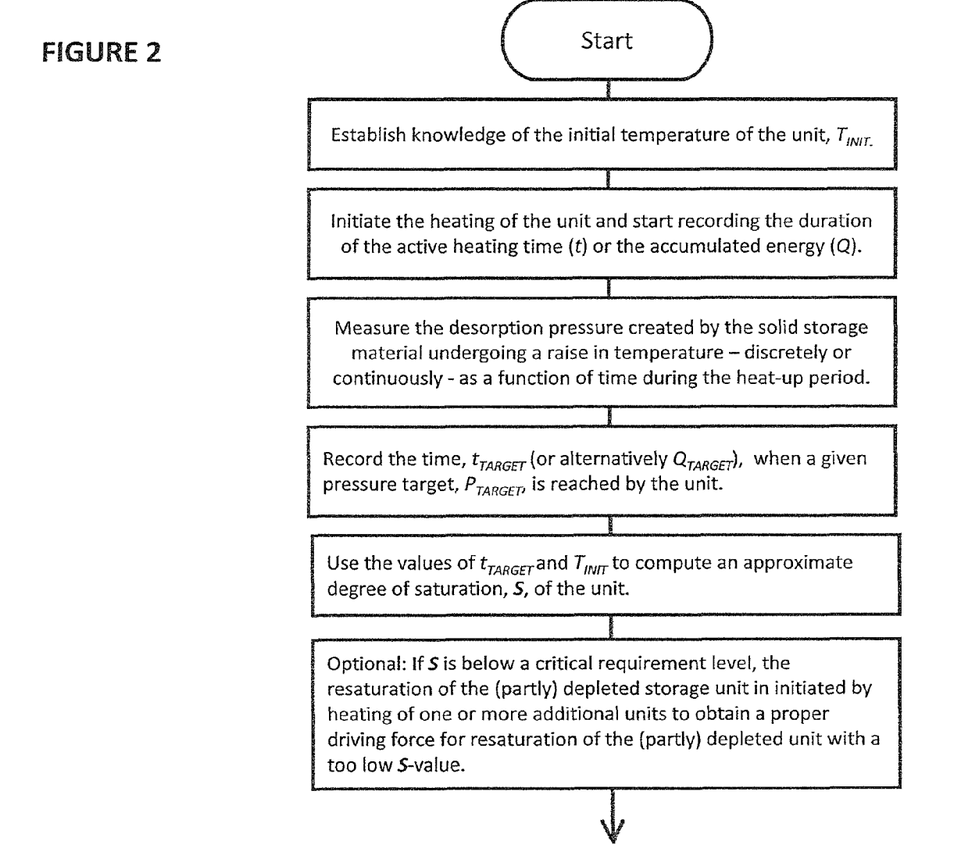
FIG. 2 shows an example of an algorithm according to the invention

FIG. 2 shows an example of an algorithm structure that can be applied during a start-up procedure. Once the values of $T_{INIT}$ and $t_{TARGET}$ are found during the start-up procedure, then S can be estimated based on a model or algorithm that uses the knowledge of the design of the storage unit (e.g. heater power, size, storage material) and/or a calculation relying on (e.g. experimental) mapping data or a look-up table.

The algorithm may additionally use the knowledge of the derived S-value to evaluate if the storage unit requires resaturation from another ammonia source—typically a larger storage unit 10 that is capable of generating ammonia pressure from a storage material 3 by thermal desorption.

Figure 3:
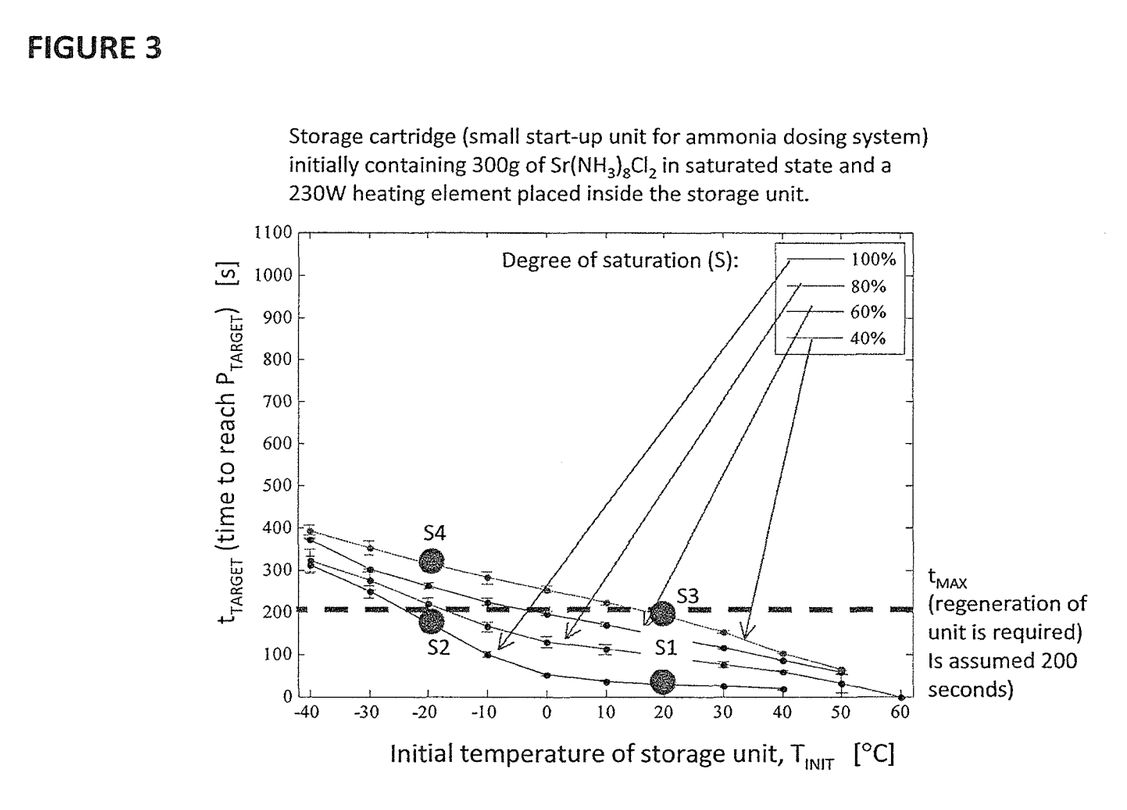
FIG. 3 shows example of experimental data verifying the capabilities of the invention with $Sr(NH_3)_8Cl_2$ as the ammonia storage material in the container.
Figure 6:
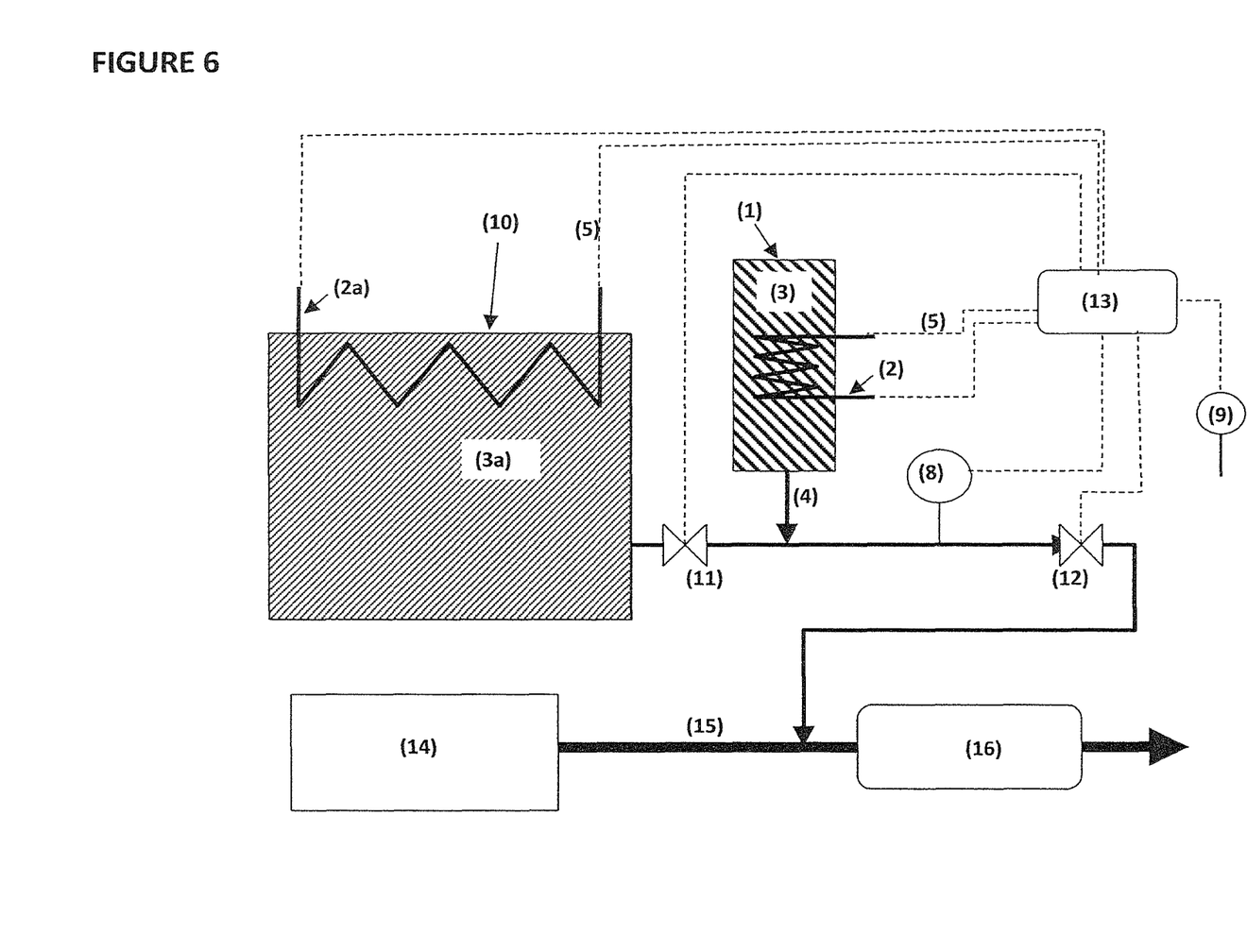
FIG. 6 schematically shows an embodiment of an entire ammonia-providing device or system, according to the invention

FIG. 3 shows one example of experimental data verifying the two-stage hypothesis of the invention. A storage unit similar to FIG. 1 has been prepared. It is a stainless steel container 1 of approx. 300 ml in size that contains a electrical heating element 2 inside powered e.g. by a 230 W power supply 5 (FIG. 6) and it contains $SrCl_2$ 6 as the ammonia absorption material directly embedded around the heater 2 and in its fully saturated state it is of the form $Sr(NH_3)_8Cl_2$ 3. The unit contains approx. 300 g material in its saturated form 3. The data shows $t_{TARGET}$ to reach $P_{TARGET}$ (3 bar absolute pressure) as a function of $T_{INIT}$ for four different levels of S. $T_{INIT}$ is measured by a standard temperature sensor 9 (FIG. 6). A dosing valve 12 (FIG. 6) may be provided to dose ammonia e.g. in the exhaust line of a vehicle. During measurement of the raise in pressure, ammonia is preferably not dosed through the dosing valve 12 to ensure that the change in pressure is only a result of heating and not a result of a raise in pressure working against a reduction is pressure caused by dosing.

The two-dimensional experimental mapping of $t_{TARGET}$ as a function of both varying S and $T_{INIT}$ has been repeated several times to be able to make confidence intervals on each of the measurement.

It is surprising that the transient operation of the system under different temperature levels and multiple resaturation phases leads to such narrow confidence intervals that allows for the envisaged concepts of the invention to be implemented. Several points on the graph, labeled S1, S2, S3 and S4 will be used in the descriptions to follow.

Figure 4:
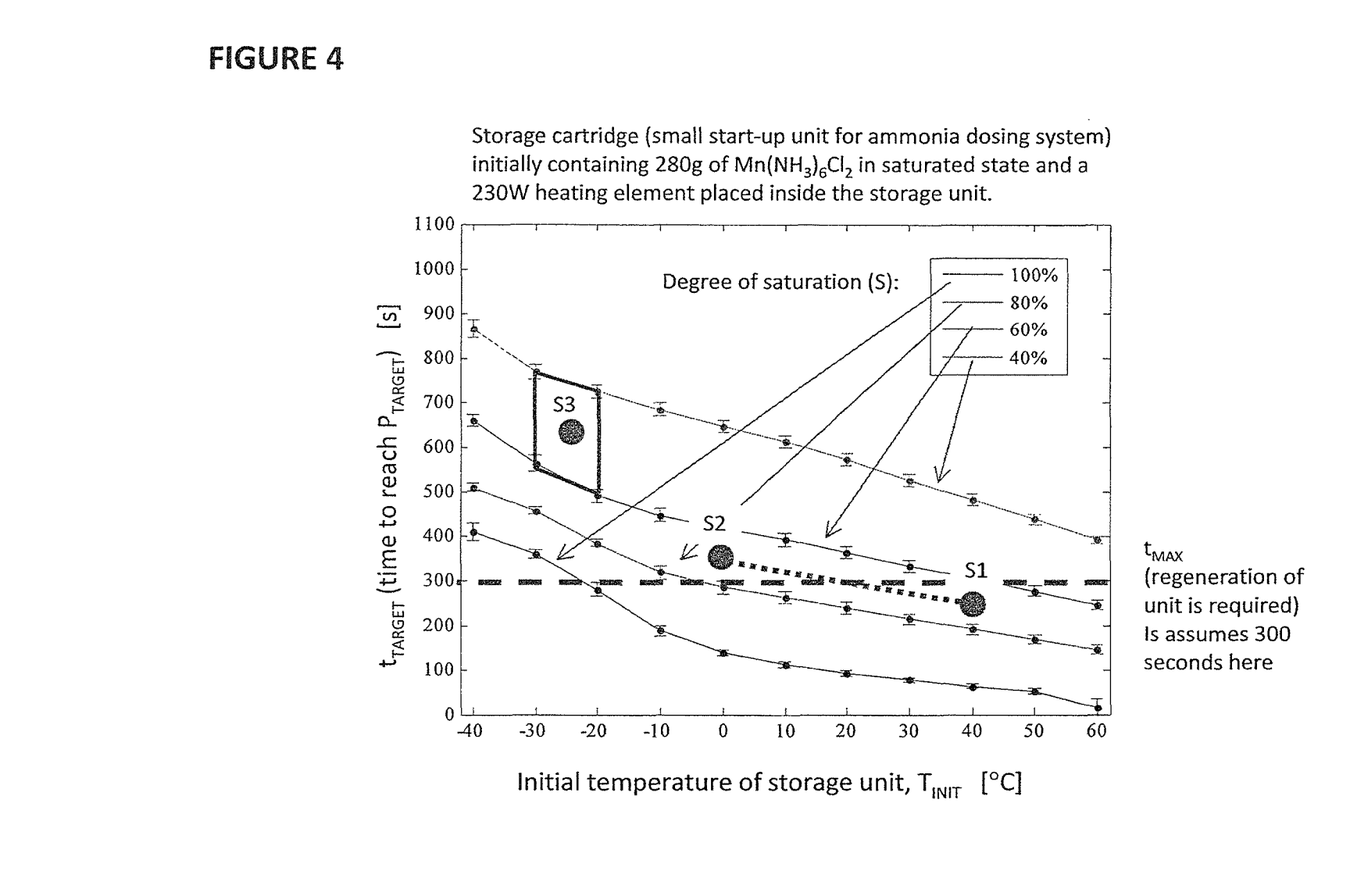
FIG. 4 shows example of experimental data verifying the capabilities of the invention with $Mn(NH_3)_6Cl_2$ as the ammonia storage material in the container.

FIG. 4 shows another example of experimental data verifying the two-stage hypothesis of the invention—but with a different material: $Mn(NH_3)_6Cl_2$. Very well-defined parameter links and narrow standard deviations are found.

While FIGS. 3 and 4 represent experimental data verifying the functionality of the invention, they also represent examples of raw mapping data that can be used in a look-up table. Both FIGS. 3 and 4 give mapping values of S in a two-dimensional space of the input parameters $T_{INIT}$ and $t_{TARGET}$. Examples of further using the mapping data are:

Creating function that describes S as a continuous surface spline function of $T_{INIT}$ and $t_{TARGET}$ and calculate S for any given combination of $T_{INIT}$ and $t_{TARGET}$ Creating interpolation functions that computes S based on the S-values of the nearest measured points of $T_{INIT}$ and $t_{TARGET}$. As an example, the point S1 on FIG. 4 gives an approximate S_value of 70% by interpolating between the two nearest measured points with $T_{INIT}$=40° C. Another example is the point S3 on FIG. 4 where the four nearest points in the box around the point $T_{INIT}$=−25° C. and $t_{TARGET}$=650 seconds are used in an interpolation to obtain an approximate level of S=50%

Creating polynomial approximation functions that can compute S based on any combination of the parameters $T_{INIT}$ and $t_{TARGET}$ The experimental data may be replaced or supplemented by a mathematical model that describes the transient warm-up dynamics of the storage unit by using parameters such as size of unit, heat capacity and heat conductivity of the storage material, the power of the heater and initial temperature to simulate a $t_{TARGET}$ value for different combinations of S and $T_{INIT}$.

Figure 5:
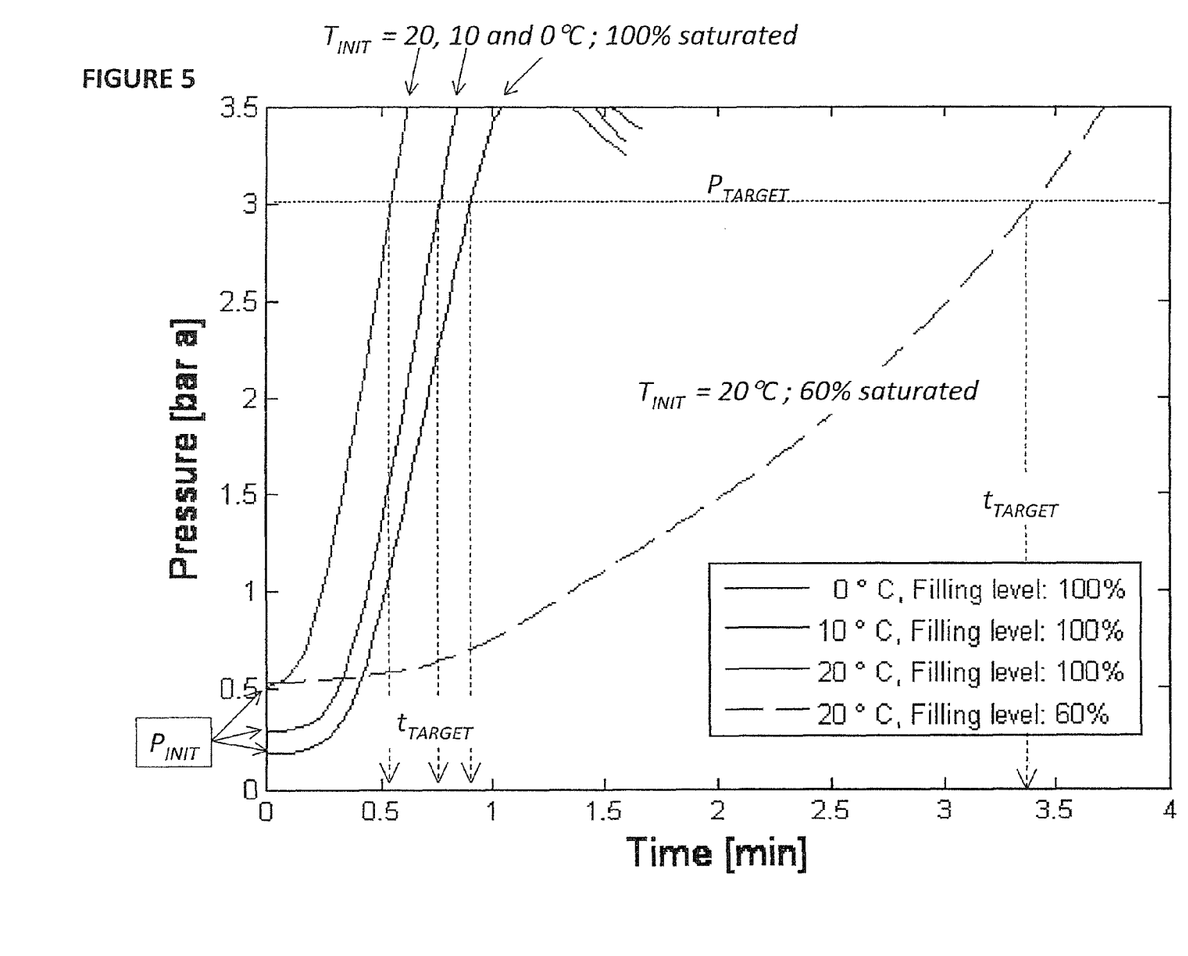
FIG. 5 shows example of specific start-up profile measurements made and analyzed according to the invention.

FIG. 5 shows some examples of the start-up phase under (varying $T_{INIT}$ and S). It can be seen that $t_{TARGET}$ is a function of both S and $T_{INIT}$—like reported in the extensive mappings of FIGS. 3 and 4. FIGS. 3 and 4 consist of a vast amount of the $t_{TARGET}$ data based on these types of curves seen on FIG. 5.

What can be seen are the different starting points on the P-axis. At very low $T_{INIT}$, the pressure before heating is closer to zero bars whereas $T_{INIT}$ at room temperature is closer to 1 bar. That enables another optional feature: When the start-up phase is initiated], $T_{INIT}$ can be used with the knowledge of the P-T relationship (e.g. van't Hoff type) for the storage material. The pressure is a function of temperature (T), i.e. P=f(T) and if $P_{INIT}$ is not close to f($T_{INIT}$), then a controller or algorithm can determine that the storage unit is above or below the temperature level of the surroundings (measured as $T_{INIT}$) and not being close to thermal equilibrium. Such an event can happen if a vehicle has been parked only for e.g. 10 minutes and then starts again. In such a situation, the warm-up profile would not have a well-defined reference point because it is warmer than the surroundings and may not result in a reliable estimation of S. The controller or algorithm may include a logical structure that chooses to discard an estimation of S when that is made under improper conditions for the applied model/mapping/look-up-table.

FIG. 2 shows an example of an algorithm structure that can be applied during a start-up procedure. At a first block, knowledge of the initial temperature of the unit, $T_{INIT}$, is established. At a second block, the heating of the unit and start recording the duration of the active heating time t or the accumulated energy Q is initiated. At a third block, the desorption pressure created by the solid storage material undergoing a raise in temperature is—discretely or continuously—measured as a function of time during the heat-up period. At a fourth block, the time, $t_{TARGET}$ (or alternatively $Q_{TARGET}$), is recorded when a given pressure target, $P_{TARGET}$ is reached by the unit. At a fifth block, the values of $t_{TARGET}$ and $T_{INIT}$ are used to compute an approximate degree of saturation, S. The computation may be carried out using a model or an algorithm describing the storage unit, and/or by (experimental or theoretical) mapping data or a look-up table, generated for this type of unit, or specifically for the individual unit considered. The sixth block shows an optional activity: If S is below a critical requirement level, the resaturation of the (partly) depleted storage unit in initiated by heating of one or more additional units to obtain a proper driving force for resaturation of the (partly) depleted unit with a too low S-value. Preferably, this method is performed in an heating-up time interval before dosing of ammonia, e.g. into the exhaust line of a vehicle, starts.

FIG. 3 shows two points, S1 and S2. As one example, during a cold start of the unit, $T_{INIT}$ is 20° C. and the time to reach target pressure is about 25 seconds. This results in mapping point S1 which intersects with the S=100% curve. Assuming that the unit always has to be able to dose within 200 seconds, an assumed value of $t_{MAX}$, when $T_{INIT}$ is above 20° C., then one can follow the S=100% curve and derive that $t_{TARGET}$ at the point S2 is still located under the 200 seconds limit. Therefore resaturation would not be required unless extended degassing is done before shutting of the ammonia release from the unit.

FIG. 4 also shows two points, marked as S1 and S2. During a cold start of the unit, $T_{INIT}$ is 40° C. and the time to reach target pressure is about 250 seconds. That places the mapping point S1, which is in between S=80% and S=60% curve, i.e. S can be interpolated to be approx. 70% (using interpolation limits the demand for extensive mapping data or size look-up table). For the example of FIG. 4, we assume that the unit always has to be able to dose within $t_{MAX}$ of 300 seconds when $T_{INIT}$ is above –0° C. (another case than FIG. 3), then one can follow the dotted interpolation path of S=70% and derive the $t_{TARGET}$ value for that level of S. It is seen that S2 will be located above $t_{MAX}$=300 seconds for expected $t_{TARGET}$ value and resaturation would thus be required.

Different combinations of requirements for allowable start-up time ($t_{MAX}$) as a function of $T_{INIT}$ can be imagined and these combinations would as examples be given by legislative demands or by the time to reach proper operating temperature of the SCR catalyst in a vehicle. This maximum allowable start-up time can be expressed in terms of a critical value of saturation, $S_{CRIT}$. Typically, $S_{CRIT}$ is not zero but it is a certain lower saturation level (e.g. chosen in the interval 5-95%) that still gives the proper dosing range functionality and start-up performance in a cold start when heating is initiated. The value $S_{CRIT}$ may also be defined as a values that gives a certain desired operating distance (or operating time) of the storage unit.

Having analyzed FIGS. 3 and 4, one can see why a method according to WO 2009/156204 A1 mentioned at the outset might have difficulties to work in real applications. FIGS. 3 and 4 show that even a small start-up unit cannot perform according to the required time-to-dose when it is empty—or even close to being empty. It is an advantage of the system to operate in a certain range of saturation degree from 100% saturated and down to e.g. 60% for some units and from 100% and down to e.g. 20% for other units. But when the unit is degassed (S being equal to or very close to 0%), the unit will have an unacceptable start-up time.

In another embodiment of the invention, the algorithm or model calculates the amount of ammonia used during operation after the start-up period and then subtracts it from the S-value obtained during the start-up period. With FIG. 3 as example, if the algorithm or controller computes that the unit has degassed ammonia corresponding to a decrease in S-value from 100% (S1) to 40% (S3), then the controller can estimate that the $t_{TARGET}$ value for $T_{INIT}$=–20° C. would be the point S4, i.e. $t_{TARGET}$ is above 200 seconds ($t_{MAX}$) and not fulfilling the performance requirements if the vehicle would be parked at this point in time and therefore the heating of the additional storage unit for resaturation the operating unit would have to be initiated.

It is also envisaged that the driving conditions of the vehicle during the start-up phase can be included in the calculation. As example, the mapping data and/or look-up table and/or mathematical model describing the storage unit takes into account the added heat loss to the surroundings caused by forced convention of heat from the exterior of the storage unit. Such a correction term may include (but not limited to) estimation of heat transfer coefficient and using surface area of the container to estimate a heat loss that may increase the $T_{TARGET}$ value beyond the value obtained if the unit was placed in still air.

It is a preferred embodiment of the invention to improve reliability of the method that there is a rather dense and coherent structure of the storage material in the container, i.e. that the heat transfer properties and heat capacities are a result of the nature of the solid material, in degassed and saturated form, and not e.g. dominated by gas-phase properties in a highly porous solid or granulated material. Preferably, the average density of the storage material in its saturated in the container form should be at least 50% of its highest theoretical maximum.

$P_{TARGET}$ may in principle have any value but it is preferred that it is higher than the absolute pressure level where the ammonia has to be dosed and higher than the equilibrium pressure of the storage material at a certain temperature level of the surroundings (e.g. measured at 40° C.). As an example, $P_{TARGET}$ could be chosen in the range from 1.1 bar to 5 bar and even more suitable a value in the range from 1.5 bar to 3.5 bar. $P_{TARGET}$ may also have different values in different intervals. As an example, for $T_{INIT}$ less than 0° C., $P_{TARGET}$ may be different from the requirements of a functional dosing pressure and therefore even be less than 1 bar (the equilibrium pressure may be significantly below 1 bar at the start of heating, e.g. 0.02 bar). For $T_{INIT}$ above 40° C., a higher $P_{TARGET}$ would be required in the look-up table or mapping data because the equilibrium pressure for some storage materials, e.g. $SrCl_2$, may already be above 1 bar before start-up heating.

In some embodiments, $P_{TARGET}$ may also be defined as a difference in pressure whereby $t_{TARGET}$ relates to the time of raising the pressure from one level in the transient to another level, e.g. from 0.8 bar to 1.8 bar. That allows accounting for the situation where a storage unit is not completely thermally equilibrated in-between use and therefore has a slightly different response to heating that a unit that has not been operated for several hours.

It is preferred that the storage material is a metal ammine complex compacted to at least 50% of the theoretical single crystal density of the material.

$SrCl_2$, $CaCl_2$, $MnCl_2$ and $MgCl_2$ or mixtures thereof are examples of desirable ammonia storage materials in their non-saturated state. Other materials such as zeolites or active carbon can be applied.

FIG. 6 shows an exemplary embodiment of a solid ammonia storage system. The invention—implemented as a method or device—is particularly advantageous for such a solid ammonia storage system used for reduction of NOx by an SCR catalyst 16 in the exhaust 15 of vehicles powered by combustion engine 14 where the storage system has one or more of the following features:

- a smaller storage unit 1 (e.g. 50 ml to 3 liter in size containing 25 g to 1.5 kg $NH_3$ stored in storage material 3), heated by electricity 2 through a power supply 5, or other means.
- one or more larger solid storage units 10 with means for heating 2a through a power supply 5 (e.g. 500 ml to 20 liters containing 400 g to 20 kg $NH_3$ stored in storage material 3a) capable of storing enough ammonia for a desired service operating interval (e.g. 25000 km).
- flow line(s) 4, temperature sensor 9, at least one pressure sensor 8 to monitor the pressure during warm-up for determining S in the smaller unit and a dosing valve 12 to control the flow of ammonia once the warm-up period is ended and functional pressure is reached.
- a controller 13 with mapping data, look-up table, models and/or algorithms according to the invention which allows for the estimation of S and the related diagnostics features relying on the knowledge of the value of S and/or using the value of S and $S_{CRIT}$ to determine when the storage unit has to be resaturated by from a different source, e.g. by heating 2 one or more of the larger storage units 10.
- a valve 11 between the one or more larger storage units 10 and the small unit 1 to avoid backflow of ammonia from a pressurized unit 1 to the larger unit 10 when the larger unit 10 is not heated and therefore has a lower pressure. The valve 11 may be an active valve that is opened by the controller but it may also be a passive valve (check valve or one-way valve).
- an engine (e.g. a diesel engine) 14 with an exhaust line 15 having a selective-catalytic-reduction chamber 16, wherein the dosing valve 12 is in fluid-communicates with the exhaust line 15 so that ammonia can be dosed into the exhaust line 15 downstream of the engine 14 and upstream of the SCR chamber 16 so that it flows in the SCR chamber 16.

In summary, what is gained by the invention is a way of estimating the saturation level of a solid storage cartridge that:

- does not require any new hardware compared to what is already implemented in the system (storage container, storage material, heater and ammonia gas connection). A temperature sensor is already—in all normal applications—placed somewhere on the system using the storage container. This temperature sensor does not have to be integrated in the storage unit, which lowers the cost of the storage unit.
- works under all required environmental conditions of e.g. vehicles, typically down to as low as −40° C.
- is orientation independent (e.g. unlike liquid level sensing systems) and may include means for taking the convection of air around the vehicle into account.
- establishes the knowledge about when it is necessary to heat an additional, larger storage unit to resaturate the smaller container. Such heating may be done by electricity from the generator of a vehicle and it has a positive influence on the fuel economy if the longest possible interval between such heating instances is obtained while still knowing that the smaller unit can perform according to demands.

The invention claimed is:

1. A method for estimating the degree of saturation of a reversible solid ammonia storage material in a storage unit, said storage unit equipped with a heater to release ammonia and a connected tube for ammonia flow in said method for determining the degree of saturation, comprising:
   a. measure the initial temperature with a sensor in or around the storage unit before any heating is initiated;
   b. initiate the heating while recording the active time of heating or the amount of energy released by the heater;
   c. measure the desorption pressure created by solid storage material in the storage unit via a pressure sensor in fluid communication with the storage unit;
   d. record the time, or the heat where the pressure reaches a certain target pressure;
   e. use the values of the target-pressure time, or the target-pressure heat, and the initial temperature to compute an approximate degree of saturation.

2. The method according to claim 1 where the storage unit is part of a system where the storage unit is a start-up unit or operational unit linked to an additional unit or additional units forming a larger storage container equipped with a heater to provide an ammonia pressure for resaturating the start-up unit or operational unit.

3. The method according to claim 1 where the integrated amount of dosed ammonia from the storage unit after the warm-up period, where the target-pressure time, or target-pressure heat was measured, is computed and subtracted from the approximate degree of saturation to have a real-time parameter for the decreasing value of the degree of saturation.

4. The method according to claim 2 where the resaturation of the fully or partly depleted storage unit is initiated by heating of the at least one additional units forming a larger storage container to resaturate the fully or partly depleted storage unit when the approximate degree of saturation or the a real-time parameter for the decreasing value of saturation degree is below a critical requirement saturation level.

5. The method according to claim 4 where the critical saturation requirement level is defined by a requirement of the storage unit to be able to deliver ammonia with a time delay shorter than that of requirements for vehicle certification.

6. The method according to claim 1 whereby computing the approximate degree of saturation is based on a model or algorithm describing the storage unit or on mapping data or a look-up table generated for the type of storage unit or specifically for the storage unit considered.

7. The method according to claim 1 wherein the approximate degree of saturation is computed by means of data which map the measured initial temperature and the recorded target-pressure time, or the recorded target-pressure heat, to a value of the degree of saturation.

8. The method according to claim 6 wherein experimental mapping data or a look-up table contains continuous or discrete values of the initial temperature and the target-pressure time, or the target-pressure heat.

9. The method according to claim 1 where the ammonia storage material capable of reversible ammonia storage is a zeolite, active carbon or a metal ammine complex or mixtures thereof.

10. The method according to claim 1 where a heater for releasing ammonia from the storage unit is placed inside the storage unit or embedded by the storage material.

11. The method according to claim 1 where value of the target pressure is chosen in the range from 1.1 bars to 5 bars.

12. The method according to claim 1 where the target pressure is not an absolute value but defined as a change from one pressure level to a higher pressure level.

13. The method according to claim 1 where a difference between the measured pressure before heating and a calculated pressure based on the initial temperature is used as a basis to discard an estimation of the approximate degree of saturation because of improper or unknown degree of thermal equilibrium between the storage unit and the surroundings.

14. A controller for a vehicle that uses solid ammonia storage material for the purpose of removing NOx by selective catalytic reduction, said controller being programmed to carry out the method according to claim 1.

15. A device for providing ammonia for an ammonia consuming unit, said device comprising:
   a storage unit with an ammonia storage material capable of reversible absorption, or adsorption, and desorption of ammonia, said unit being equipped with a heater to release ammonia by desorption;
   a pressure sensor to determine the pressure in the storage unit;
   a temperature sensor to determine an initial temperature;
   a controller that is programmed to carry out the method according to claim 1.

16. The device according to claim 15 where the device contains one or more additional storage units equipped with a heater and said heater being arranged to provide ammonia pressure to partly or fully resaturate the storage unit when the approximate degree of saturation has reached a lower threshold value.

* * * * *